United States Patent
Scott (12)

(10) Patent No.: US 6,291,528 B1
(45) Date of Patent: *Sep. 18, 2001

(54) PROSTAGLANDIN $E_1/F_2$ IN COMBINATION WITH PROSTAGLANDIN $F_{2\alpha}$ FOR ENHANCING FEMALE SEXUAL AROUSAL

(76) Inventor: Nathan Earl Scott, 610 Laguna Rd., Fullerton, CA (US) 92835

( * ) Notice: Subject to any disclaimer, the term of this patent is extended or adjusted under 35 U.S.C. 154(b) by 0 days.

This patent is subject to a terminal disclaimer.

(21) Appl. No.: 09/422,031

(22) Filed: Oct. 20, 1999

Related U.S. Application Data

(63) Continuation-in-part of application No. PCT/US98/26609, filed on Dec. 15, 1998, which is a continuation-in-part of application No. 09/038,378, filed on Mar. 11, 1998, now Pat. No. 5,962,528, and a continuation-in-part of application No. 09/005,087, filed on Jan. 9, 1998, now abandoned, and a continuation-in-part of application No. 08/992,946, filed on Dec. 18, 1997, now Pat. No. 5,981,593, each is a continuation-in-part of application No.08/090,483, filed on Jul. 12, 1993, now Pat. No. 5,708,031, which is a continuation of application No. 07/860,107, filed on Mar. 30, 1992, now abandoned, which is a continuation of application No. 07/725,350, filed on Jul. 3, 1991, now abandoned.

(51) Int. Cl.$^7$ ............................................. A61K 31/5575
(52) U.S. Cl. ............................................................. 514/573
(58) Field of Search ................................................ 514/573

(56) References Cited

U.S. PATENT DOCUMENTS

| | | | |
|---|---|---|---|
| 3,917,864 | 11/1975 | Karim | 424/305 |
| 4,311,707 | 1/1982 | Birnbaum et al. | 424/305 |
| 5,242,391 | 9/1993 | Place et al. | 604/60 |
| 5,482,039 | 1/1996 | Place | 128/653.1 |
| 5,773,457 | 6/1998 | Nahoum | 514/397 |
| 5,877,216 | 3/1999 | Place et al. | 514/573 |

FOREIGN PATENT DOCUMENTS

| | | |
|---|---|---|
| 0357581 | 8/1989 | (EP) . |
| 9116021 | 10/1991 | (WO) . |
| 9300894 | 1/1993 | (WO) . |

*Primary Examiner*—Phyllis G. Spivack
(74) *Attorney, Agent, or Firm*—Koppel & Jacobs; Michael J. Ram

(57) ABSTRACT

A method of treating and a composition for treating female sexual arousal dysfunction, comprising administering to the patient a unit dose of a formulation comprising an effective amount of a prostaglandin, selected from prostaglandin $E_1$, prostaglandin $E_2$, pharmaceutically acceptable salts thereof and physiologically acceptable esters thereof, wherein the prostaglandin is formulated with prostaglandin $F_{2\alpha}$, together with a pharmaceutically acceptable delivery medium and/or a lubricant.

17 Claims, 3 Drawing Sheets

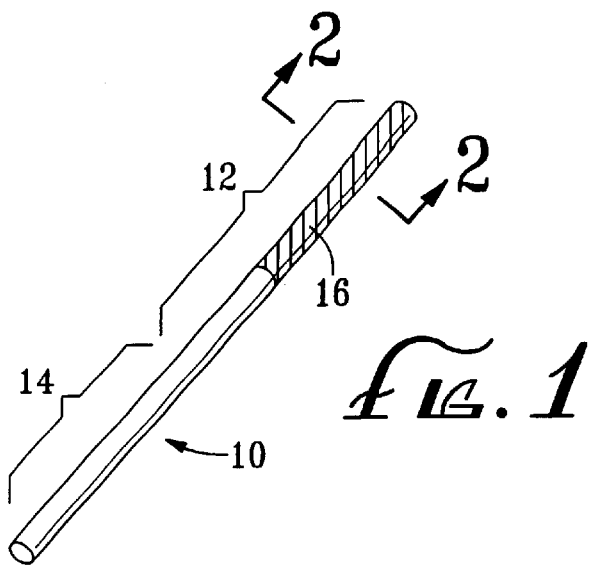
Fig. 1
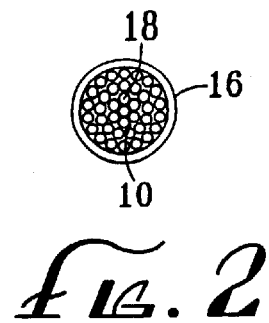
Fig. 2
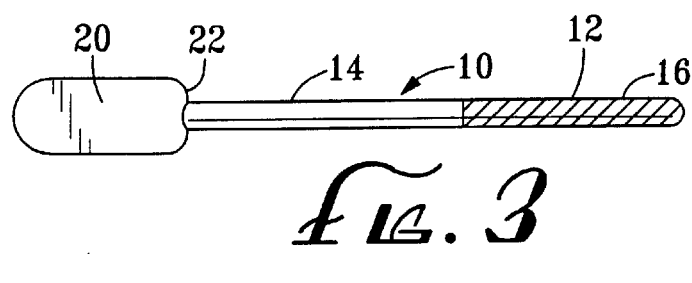
Fig. 3
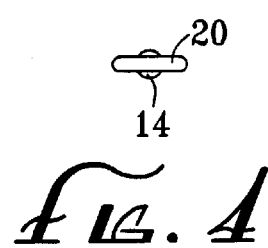
Fig. 4
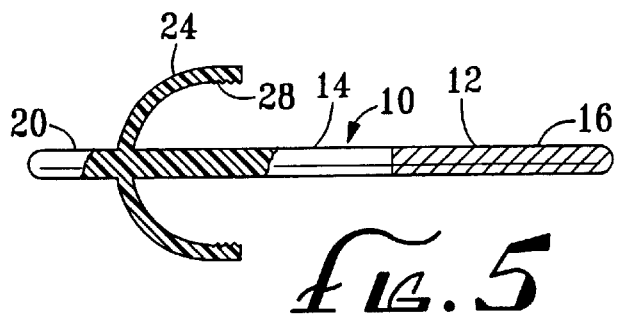
Fig. 5
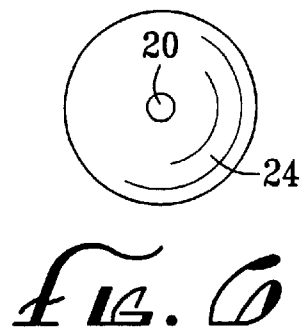
Fig. 6
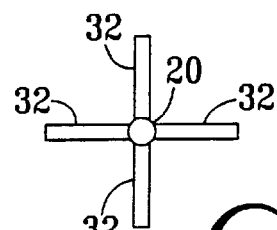
Fig. 7

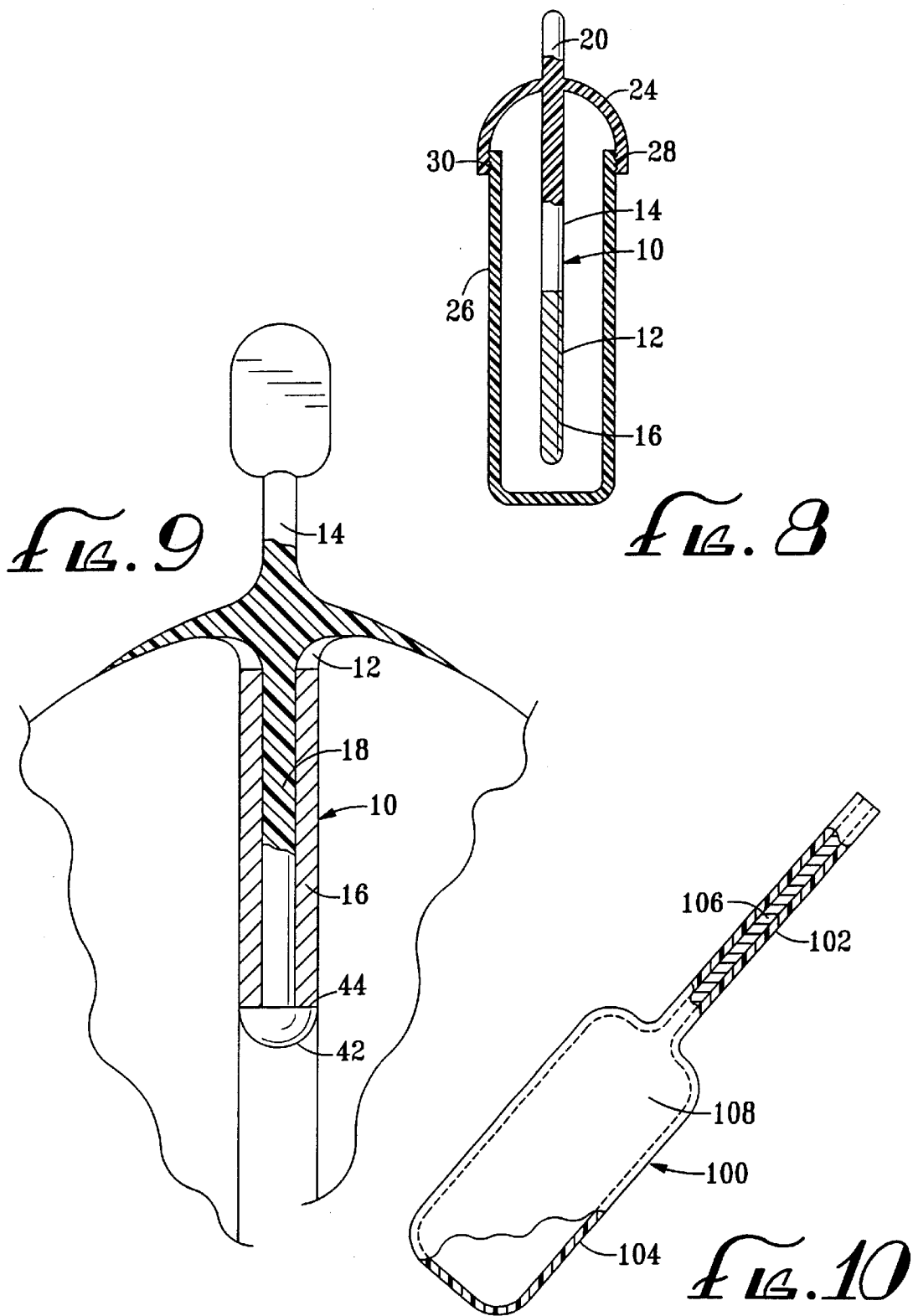

PROSTAGLANDIN E₁/F₂ IN COMBINATION WITH PROSTAGLANDIN F$_{2\alpha}$ FOR ENHANCING FEMALE SEXUAL AROUSAL

AREA OF THE ART

This application is a continuation-in-part of PCT/US98/26609 filed Dec. 15, 1998, said application designated as a continuation-in-part in the U.S., which is a continuation-in-part of and claims priority based on U.S. Ser. No. 09/038,378 filed Mar. 11, 1999 now U.S. Pat. No. 5,962,528, U.S. Ser. No. 09/005,087 filed Jan. 9, 1998, now abandoned and U.S. Ser. No. 08/992,946 filed Dec. 18, 1997 now U.S. Pat. No. 5,981,593, all of which are continuations-in-part of Ser. No. 08/090,483 filed Jul. 12, 1993, now U.S. Pat. No. 5,708,031 issued Jan. 13, 1998 which is a continuation of Ser. No. 07/860,107 filed Mar. 30, 1992 now abandoned, which is a continuation of Ser. No. 07/725,350 filed Jul. 3, 1991 now abandoned.

BACKGROUND OF THE INVENTION

The present invention relates to the treatment of impotence in males, enhancement of sexual arousal in females and devices for delivering pharmaceutical compositions to treat impotence in males and sexually stimulate females. In particular, the invention relates to the use of prostaglandin PGE₁ or PGE₂ in combination with PGF$_{2\alpha}$ in the treatment of sexual dysfunction.

In excess of about 10 million men in the United States alone exhibit sufficient erectile dysfunction that they can be characterized as effectively impotent. A significant number of men additionally suffer from an inability to develop an erection which may not meet the clinical definition of impotence but may not be satisfactory to their desires or those of their partner to provide mutually satisfactory sexual intercourse. Impotence in the human male can arise from a variety of psychological and physiological etiologies. For example, long term diabetes, damage to the spinal cord, multiple sclerosis, or nerve damage resulting for example from lower abdomen or prostate surgery, and advancing age can result in impotence. Additionally, there are psychological causes for impotence. For differing reasons, each of the foregoing result in an inability to pressurize the corpora cavernosa. which can result in turn from either an insufficient arterial inflow on the supply side, or an insufficient increase in the venous output resistance to blood flow.

A wide variety of mechanical means have been provided, in an effort to overcome erectile dysfunction. For example, U.S. Pat. No. 4,596,242 to Fischell discloses a surgically implantable hydraulic system, having a fluid reservoir and pressure generator, a patient manipulable valve, a pressure reservoir and a distensible member responsive to actuation of the valve. A variety of other prior art mechanical implants and other devices for this purpose are described in the Background of the Invention section of the U.S. Pat. No. 4,596,242.

In addition to the mechanical efforts to overcome erectile dysfunction, pharmaceutical approaches have been tried as well. For example, prostaglandin E₁ has been observed to produce erection in some cases, by direct percutaneous injection into the penis or as a meltable pellet placed in the urethra (U.S. Pat. Nos. 5,773,020; 5,474,535; 5,242,391). PGE₁, in a drug composition known as "trimix", has also been injected directly into the corpus cavemosa to treat impotence. One of the additional ingredients in trimix to phentolamine mesylate.

Most recently Pfizer has made sildenafil citrate available in oral dosages as a treatment for impotence under the trade name, Viagra®. However, Viagra® is counter indicated for use by men with cardiac disease, death in cardiac patients during or following intercourse has been indicated as a possible side effect, and interaction with nitroglycerine may cause immediate death. In addition, a new warning has been added to labeling for Viagra® warning of a possible occurrence of priapism. Also since sildenafil citrate is administered orally, the effect of the drug is systemic and not restricted, as in direct delivery to the penis, to a localized response.

Further, both PGE₁ and Viagra® have been shown to be effective in only certain causes of impotence. In particular, neither drug appears to be particularly effective to treat impotence resulting from surgical procedures on the prostate.

Still further, the needs for localized drugs to treat female sexual deficiencies have not been adequately addressed by presently available products. It is estimated that there are ten million women in the United States who suffer from female sexual arousal dysfunction.

Therefore, there remains a need for an improved treatment of erectile dysfunction in the male and arousal dysfunction in the female. Surgical implantation and/or repeated injections range from disfavored to medically disadvantageous, and do not, as a whole, provide a satisfactory solution to the problem. From a patient usability standpoint, erectile dysfunction would most advantageously be treated on a self-administration basis, without the need of surgical intervention or repeated injections of a pharmaceutical agent. This problem has been addressed by the use of PGE₂ as claimed in my U.S. Pat. No. 5,708,031. However, some patients on using urethral placement of PGE₂ materials have experienced urethral burning and cavernous sinus aching within the genital area. This unpleasant sensation is also experienced on use of PGE₁. To counteract this side effect an anesthetic may be added to the prostaglandin formulation. However, this in turn requires using an increased quantity of the prostaglandin.

Further, the prior gel formulation and the PGE₁ pellet requires the delivery of a greater volume of treatment composition than may be desired. Still further, it would be a significant improvement if a simple and safe composition is available for application to the female external genitalia which would increase sensitivity, enhance lubrication and result in local vasodilation and engorgement of external and meatal tissue all of which would enhance the female sexual arousal and experience.

Therefore, there is a need for a PGE₂ formulation which avoids these negative sensations but does not interfere with the effectiveness of the PGE₂ for treatment of impotence.

SUMMARY OF THE INVENTION

In accordance with one aspect of the present invention, there is provided method of treating erectile dysfunction in a male patient, comprising the step of administering to the patient a unit dose of a formulation comprising an erectile dysfunction treating amount of prostaglandin E₂ compound, or pharmaceutically acceptable salts or derivatives thereof. The prostaglandin E₂ compound is preferably formulated together with a pharmaceutically acceptable delivery medium, which may comprise local anesthetic agents and/or a lubricant. Preferably, the anesthetic agent comprises lidocaine. The dose of PGE₂ may be in the form of a urethra sized suppository meltable at body temperature, coated on a removable wand, carried on and/or in a porous, non-absorbable wand sized for easy placement into and withdrawal from the urethra, or in physiologically acceptable carrier (saline or water) placed in the urethra via a small diameter tube. The prostaglandin $E_2$ compound can also be formulated with a small amount of prostaglandin $F_{2\alpha}$ and/or phentolamine mesylate together with a pharmaceutically acceptable delivery medium and/or a lubricant.

A unit dose of the formulation in accordance with the present invention will typically be less than about 5 cc in volume, preferably less than about 3 cc and most preferably below about 1 cc. The amount of active ingredient in a unit dose will typically be within the range of from about 0.1 mg to about 4.0 mg. More preferably, the amount of prostaglandin $E_2$ in a unit dose will be within the range of from amount 0.6 mg to about 3.6 mg, depending on the cause and severity of the erectile dysfunction or arousal deficiency. This may be more than the amount of $PGE_1$ required for a beneficial result. However, tests show that the results obtained from use of $PGE_1$ are much less satisfactory than when $PGE_2$ is used. Further, if anesthetic, such as lidocaine is added to the formulation to minimize or eliminate burning, 1.2 mg to about 3.6 mg of $PGE_2$ may be required. It has now been found that adding prostaglandin $F_{2\alpha}$ in amounts of about 0.1 micrograms (0.1 µg) to about 2.0 µg to either prostaglandin $E_2$ or $E_1$ formulations prevents the burning and aching without noticeably interfering with effectiveness of the prostaglandin. A preferred amount is 0.25 µg of $PGF_{2\alpha}$ per 1 mg of $PGE_2$. It has also been found that adding phentolamine mesylate to this composition further increases the effectiveness of the composition (increased rigidity and increased but controlled longevity).

The administration step of the method in accordance with the present invention comprises the transurethral administration of the unit dose of formulation. In an embodiment where the formulation comprises a cream, gel form or saline solution, the formulation is preferably transurethrally instilled or inserted such as by extrusion through syringe or unit dose administration packet comprising an elongate tubular administration tip.

For female arousal, it has been found that delivery of the composition to the external female genitalia, the internal mucosal membrane or into the female urethra has a significant arousal effect.

An alternative delivery procedure comprises the transurethral placement of a unit dose of the formulation using a coated wand or a suppository containing a quantity of the formulation suitable for delivery to the patient within a preset period of time.

In an embodiment of the present invention, wherein the administrable form of the formulation comprises a relatively rigid suppository, the suppository can be manually inserted into the distal opening of the urethra.

A further embodiment provides for urethral insertion of a removable wand, which may be porous, which carries the unit dose in a form which transfers over a controlled period of time through the urethral mucosa.

These and further objects and advantages of the present invention will become apparent from the Drawings and Description which follows, considered together with the appended Claims.

DRAWINGS

These and other features, aspects and advantages of the present invention will become better understood with reference to the following description, appended claims, and accompanying drawings, where:

FIG. 1 is a perspective side view of a first version of the insertable drug delivery device.

FIG. 2 is a cross sectional view taken along line 2—2 of FIG. 1.

FIG. 3 is a side view of a second version of the insertable drug delivery device.

FIG. 4 is an end view of the second version of the insertable drug delivery device.

FIG. 5 is a side view of a third version of the insertable drug delivery device.

FIG. 6 is an left end view of the third version of the insertable drug delivery device.

FIG. 7 is an left end view second variation of the third version of the insertable drug delivery device.

FIG. 8 is a cut away side view of the third version of the insertable drug delivery device of FIG. 6 inserted in a carrier.

FIG. 9 is a cut away side view of a variation of each of the above versions inserted in a penis.

FIG. 10 is a partial cutaway view of a device for delivery of a liquid dose of impotence treating drug.

DETAILED DESCRIPTION OF PREFERRED EMBODIMENTS

Figure 11:
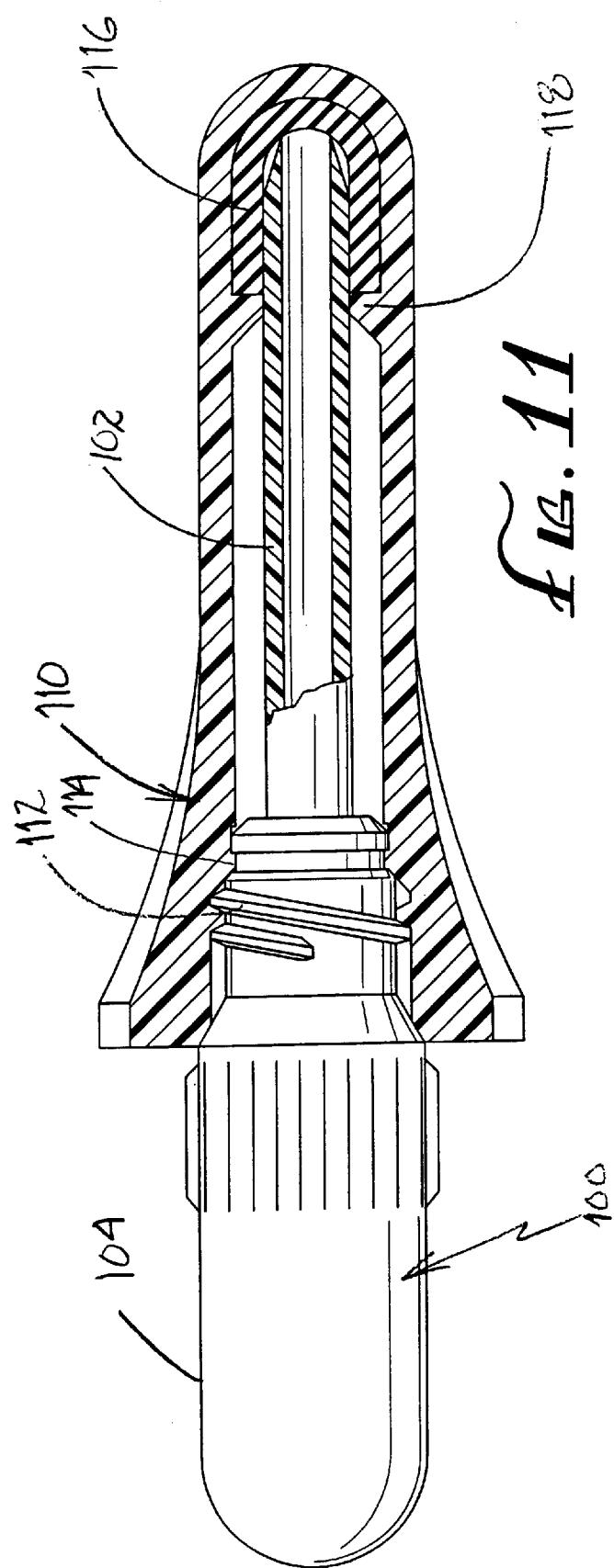
FIG. 11 is a partial cutaway view of the device of FIG. 10 enclosed in a liquid tight cap.

The prostaglandins are a series of cyclic derivatives of certain unsaturated fatty acids. They are found in a variety of tissues, including the prostate gland, the seminal vesicles, the lungs and the brain. These naturally occurring prostaglandin are derived by cyclization of 20-carbon unsaturated fatty acids such as arachidonic acid. See Lehninger, Albert L., *Biochemistry*, 2d ed. (1975), p. 300 (hereinafter "Lehninger").

Carbon atoms of the fatty acid backbone are cyclized to form a characteristic 5-membered ring. The prostaglandin are divided into a number of groups, including those designated A–F, based on the configuration of the ring structure. Prostaglandin also differ in stereochemistry and in the number of side chain double bonds which are conventionally indicated by a subscript number. Thus, for example, prostaglandin $E_2$ ("$PGE_2$") has the ring configuration characteristic of the E group and contains two side chain double bonds. The chemical name for $PGE_2$ is (5Z, 11α, 13E, 15S)-11, 15-Dihydroxy-9-oxo-prosta-5, 13-dien-1-oic acid and the structural formula of one form is represented in Formula I, below. The molecular formula is $C_{20}H_{32}O_5$.

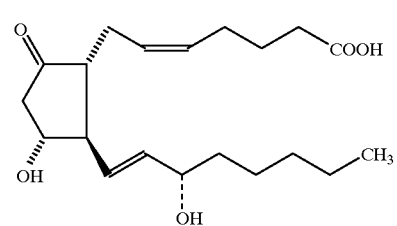

I

The biosynthesis of prostaglandin has been well characterized. See, e.g., Lehninger at p. 687. In a typical biosynthetic pathway, exemplified by production of $PGE_2$, the essential fatty acid linoleic acid is converted into the 20-carbon arachidonic acid, which is then acted upon by prostaglandin synthase, doxygenase enzyme. Oxygen atoms are added at carbon atoms 9 and 15, and the product is cyclized by formation of a bond between carbon atoms 8 and 12. In the presence of reduced glutathione, this synthesized product undergoes conversion into prostaglandin $PGE_2$. Other types of naturally occurring prostaglandins are derived from different polyunsaturated fatty acids.

In about the 1960's, prostaglandin were isolated from a particular species of Caribbean coral, which made them more widely available for research. Catanzarite, Valerian A. and Gary Aisenbrey, *Contemporary OB/GYN* (October 1987), p. 22 (hereinafter "Catanzarite"). A large number of natural and synthetic analogues of he prostaglandin are now known. Lehninger at 687.

Kock (Published PCT Application WO 90/02542, Mar. 22, 1990) describes the treatment of male impotence by delivery of 10–220mg of phentolamine or 50–300mg phenoxybenzamine to the male urethra. Alternative materials comprise other $\alpha_1$, and $\alpha_2$ blocking agents vasoactive intestinal polypeptides, prostaglandins ($PGE_1$, $PGE_2$ and $PGF_2$) and nitroglycerine. A corresponding US patent (U.S. Pat. No. 5,886,039) issued Mar. 23, 1999. Kock clearly did not understand the distinctly different clinical response to the various prostaglandins and that certain prostaglandins, such as $PGF_{2\alpha}$, as described herein below, actually function in a completely opposite manner and can not be used to cause an erection in males.

The various different prostaglandins are known to produce often unpredictable effects over a very wide range of biological activities of a hormonal or regulatory nature. Prostaglandin have been reported to both lower and raise blood pressure, to inhibit gastric secretion, dilate bronchi, inhibit lipolysis, antagonize vasopressin-induced antidiarrhesis, constrict the pupil, increase and decrease the intraocular pressure and produce contraction of the uterus. See, e.g, Ganong, William F., *Review of Medical Physiology*, 7th ed. (1975), p. 226 (hereinafter "Ganong"). The naturally occurring prostaglandin all appear to be capable of affecting the control of vascular and other smooth muscle contractions. In the central nervous system, prostaglandin are known to modify responses to certain synaptic transmitters. They have been reported to mimic the actions of some hormones and to inhibit the actions of certain others. See Ganong at 226.

Two of the most extensively studied of the prostaglandin are $PGE_2$, and $PGF_{2\alpha}$. Both of these molecules are synthesized within the pregnant and non-pregnant uterus. While $PGE_2$ and $PGF_{2\alpha}$ are similar in mediating some effects, they are different with respect to certain others. Both cause uterine contractions, but they predominate at different sites within the uterus—$PGE_2$ in the lower uterine segment, $PGF_{2\alpha}$ is more important in generating uterine contractions. $PGE_2$ elevates body temperature, whereas $PGF_{2\alpha}$ has no apparent effect on body temperature. $PGE_2$ is a vasodilator and bronchodilator, while $PGF_{2\alpha}$ is a bronchoconstrictor and vasoconstrictor. (See Catanzarite at 21–22.)

Prostaglandin have been used in gynecology for pregnancy termination. Preparing the cervix with prostaglandin suppository has been found to reduce the incidence of cervical laceration and significant bleeding (Catanzarite at 22). Synthetic analogues of prostaglandin $PGE_2$, such as 16-16-dimethyl $PGE_2$ and 9-methylene $PGE_2$, have proven useful for the induction of first trimester abortions. Such procedures typically use vaginal suppositories containing 20 milligrams $PGE_2$ or 3 milligrams 15-methyl $PGF_{2\alpha}$, or by repeated intramyometrial injections of 15-methyl $PGF_{2\alpha}$, or by infusing a $PGF_{2\alpha}$, -urea mixture (20 milligrams of $PGF_{2\alpha}$ and 40 milligrams of urea in 100 Ml of 5% dextrose in water) into the amniotic sac.

In obstetrics, prostaglandin have been used for cervical ripening, labor induction and control of post-partum hemorrhage (Catanzarite at 29). For cervical ripening, $PGE_2$ had been given intravenously, orally and vaginally, but the preferred route is intracervically. A $PGE_2$ gel is now commercially available in Scandinavia, and another $PGE_2$, gel is being investigated in the United States. The $PGE_2$ gel can also be used for labor induction (3–5 mg of $PGE_2$, prepared by blending a 20 mg suppository with 60 mL of lubricating jelly and using 9–15 mL of the mixture, is placed in the vagina) (Catanzarite at 32). Prostaglandin have also been utilized to control post-partum hemorrhage.

Since circulating prostaglandin can be rapidly metabolized in the lungs, liver and kidneys, a number of synthetically modified prostaglandins have been developed that are not metabolized as quickly (See, e.g., Catanzarite at 32).

Prostaglandin $PGE_2$, also known as the "Prostin $E_2$" brand of "dinoprostone," is available from Upjohn Company in the form of a vaginal suppository. Indications and usage reported by Upjohn are (i) termination of pregnancy from the 12th through the 20th gestational week, (ii) evacuation of the uterine contents in the management of missed abortion or intrauterine fetal death up to 28 weeks of gestational age, and (iii) in the management of non-metastic gestational trophoblastic disease (benign hydatidiform mole). See The Upjohn Co., Prostin $E_2$ product description 810 994 009, October, 1990.

$PGE_2$ is also available from several sources as a purified, freeze dried or lypholized product which is readily soluble in saline or distilled water.

Contraindications to the use of prostaglandin $PGE_2$ include hypersensitivity to dynoprostone, acute pelvic inflammatory disease, or patients with active cardiac pulmonary renal or hepatic disease. Upjohn notes that although carcinogenic bioassay studies have not been conducted in animals for $PGE_2$ (because of the limited indication for use and the short duration of administration), there was no evidence of mutagenicity in either the Micronucleus Test or in the Ames Assay. Upjohn also indicates that a number of adverse reactions may be observed with the use of $PGE_2$ for abortions. These adverse reactions are related to the contractile effect of $PGE_2$ on smooth muscle and include vomiting, temperature elevations, diarrhea, nausea, transient diastolic blood pressure decreases, and a number of other effects. Upjohn's vaginal suppository contains 20 mg of $PGE_2$ in a mixture of glycerides of fatty acids.

Upjohn markets a (15S)-15-methyl analogue of prostaglandin $PGF_{2\alpha}$ under the brand name Hemabate®, also known as "carboprost tromethamine sterile solution." The structural formula of Hemabate is represented in:

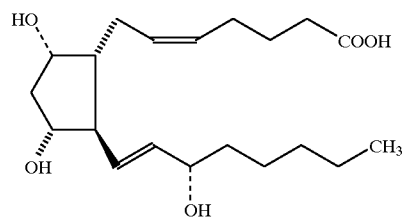

Upjohn reports that Hemabate® is indicated for aborting pregnancy between the 13th and 20th weeks of gestation, in certain conditions related to second trimester abortions, and in the treatment of post-partum hemorrhage. See The Upjohn Co., product descriptions 814 350 002, November, 1989. For abortion, the prostaglandin solution is injected using a syringe and administered deep in the muscle. Intramuscular injection is also used for treating post-partum uterine bleeding.

Upjohn also markets prostaglandin $PGE_1$, as the "Prostin VR Pediatric" brand of "alprostadil sterile solution," which is used to temporarily maintain the patency of the ductus arteriosis until corrective surgery can be performed in neonates having congenital heart defects and who depend upon the patent ductus for their survival. For the administration of $PGE_1$ in neonates, Upjohn recommends continuous intravenous infusion into a large vein, or administration through an umbilical artery catheter placed at the ductal opening. See The Upjohn Co., product description 811 987 004, in Physicians Desk Reference, 45th Edition, p.2250 (1991).

Quite surprisingly, the inventor herein has discovered that transurethral application of $PGE_2$ can in many cases provide an effective, reversible treatment of erectile dysfunction in human males. Thus. in accordance with one embodiment of the present invention, $PGE_2$ or a pharmaceutically acceptable salt, ester or other derivative thereof is formulated together with a carrier medium which may comprise any of a variety of additional excipients or adjuvants into a form suitable for transurethral delivery. One approach is to apply the composition to a wand, which may be either porous or non-porous, in sufficient quantities so that the desired dosage is released and absorbed through the mucosa of the urethra when the coated wand is placed in the urethra. When an erection of the desired tumescence is obtained the wand is then removed, terminating delivery of the composition, thus significantly reducing the possibility of overdosing. While the formulation may be provided in the form of a meltable suppository, such a delivery means is unsuitable for removal to terminate delivery of the composition and can result in overdosing as well as the delivery of excess $PGE_2$ to the vagina of the partner.

In a second embodiment a suitable amount of a freeze dried $PGE_2$ is dissolved in physiological saline or sterile water and placed within the urethra using a short, small diameter catheter. The $PGE_2$ absorption is rapid with an erection, ensuing within 3–5 minutes, persisting for 1–2 hours depending on dosage. However, alternative replacements for the water carrier include creams or gels which can flow at or above room temperature, for example at body temperature.

In accordance with another aspect of the present invention, there is provided an antidote for reversing the effects of the foregoing $PGE_2$ treatment, comprising administration of an antidotal amount of $PGF_{2\alpha}$, or pharmaceutically acceptable salts, esters or derivatives thereof Preferably, 15-methyl $PGF_{2\alpha}$ is utilized for this purpose. This antidote can be delivered in the same manner as discussed above.

Preferably, the $PGE_2$ or $PGF_{2\alpha}$ or combination of $PGE_2$ and $PGF_{2\alpha}$ with or without other additives, as discussed below, will comprise a cream, gel, or water based solution although a more solid form such as pellets or a rod-shaped suppository body may also be used. In the following described devices or delivery techniques, in each case where $PGE_2$ is referred to, it is contemplated that the $PGF_{2\alpha}$ may be substituted for delivery purposes, These devices are also applicable to delivery of $PGE_1$ compositions or other impotence treatment drugs.

Administration of the liquid, cream or gel form may be accomplished by transurethral delivery using a syringe without a needle, or with a short blunt cannula attached. The liquid, gel or cream forms are preferably provided in unit dose amounts for self administration by the patient. For this purpose, compressible unit dose packages are preferably provided with an elongate tubular delivery spout, sized for transurethral insertion. Following transurethral installation of any of the liquid, gel or cream forms, the distal end of the urethra is preferably occluded, such as by manual pressure for up to several minutes, to permit sufficient dwell time for absorption.

A typical male urethra in a flaccid penis is from about 2.5 cm to about 8 cm and the typical diameter of the urethra is from about 1 mm to about 3 mm. Accordingly, the wand with $PGE_2$ and/or $PGF_{2\alpha}$ applied has a diameter approximating the urethra diameter or slightly larger so that the outer surface of the wand is in intimate contact with the mucosal lining of the urethra or swells when inserted. The typical length of the insertable portion of the wand is from 20% to 90% of the patients' urethra in the flaccid state, preferred 25%–40% with some or all of the insertable portion coated with $PGE_2$. The wand also has an external portion or length for grasping between the users fingers for placement and removal. This portion may be of a larger diameter or a flange may be positioned between the insertable portion and the exterior portion to prevent the wand from being inserted too far into the urethra.

For delivery of the $PGE_2$ dissolved in saline or sterile water, solution, a catheter of about 1.5–3 mm in diameter, possibly with a narrowed insertion tip or narrowed internal diameter to facilitate the delivery of a spray, is inserted into the urethra 0.5 to 2 cm and a bolus or spray of about 0.1 cc to 1 cc of a solution containing 0.1 to 4.0 mg $PGE_2$ is placed in the urethra.

A first embodiment of the drug delivery device, shown in FIG. 1, comprises a wand 10 which is sized to be placed within the urethra of the penis. The wand has an insertable portion 12 which, in use, resides in the urethra, and a holding portion 14 for grasping by the user during insertion. The insertable portion 12 has a partial or complete covering of $PGE_2$ in a suitable carrier 16.

FIG. 2 shows the wand 10 in cross section. The wand is shown as porous, with pores 18, the $PGE_2$, with or without a carrier, 16 being both on the surface of the wand 10 and in the pores 18. The invention contemplates a nonporous wand 10 with the $PGE_2$ and carrier coated only on the surface as well as an alternate porous version with the $PGE_2$ and carrier being on both the surface as well as in the pores. The porous version allows delivery of more drug to the patient. However, because some of the drug is within the pores, the delivery rate for that portion may be slower than for the $PGE_2$ in the surface coating.

A second embodiment of the drug delivery device, shown in FIGS. 3 and 4, in addition to the features shown in FIGS. 1 and 2, has a handle 20 for grasping by the user during insertion and removal of the device. The shoulder 22 prevents the wand from being inserted too deeply.

A third embodiment, shown in FIGS. 5 and 6, instead of the shoulder 22, has a cap 24 to prevent insertion of the wand 10 to a depth greater than desired. In FIG. 5, the cap is shown to have a curved profile similar to the rounded shape of the head of the penis. However, any shape is usable as long as the width of the cap is greater than the diameter of the urethra so as to prevent insertion of more than the desired length. FIG. 6 shows the cap 24 as hemispherical in shape so that it can also serve as a cap to close a carrying container 26, such as shown in FIG. 8. In the particular embodiment shown in FIGS. 5, 6 and 8, the cap 24 has threads 28 on its lower surface which can interact with similarly disposed threads 30 on the outer upper end of the container 26. In this manner the drug containing wand 10 can be inserted in the container 26 and closed and sealed, such as by a sonic or heat weld, to keep the $PGE_2$ from contamination or dissipation. It is also contemplated that the threads 28 can be replaced by other sealing means such as snap rings or a friction fit, each of which may be further sealed by an externally applied adhesive tape (not shown).

FIG. 7 shows a further variation of the embodiment of FIG. 5 wherein the cap 24 is replaced by one or more extensions 32 which radiate outward from the wand 20 at the juncture of the insertable portion 12 and the holding portion 16. FIG. 7 shows four extensions 32 which can be extended perpendicular to the wand 10 surface to be curved as in FIG. 5.

FIG. 9 is an enlarged cut away view showing a further embodiment of the $PGE_2$ delivery device incorporating features shown in FIG. 7 placed within the male urethra. The porous wand 10 has the $PGE_2$ material in a suitable carrier 16 coated on the surface and in the pores of the wand. The insertion end of the wand 10 has a rounded tip 42 which has a diameter which approximates the diameter of the urethra. A length of the inserted portion 12 is coated with the $PGE_2$ and carrier composition 16, the composition or the $PGE_2$ alone also being carried in the pores 18 of the wand 10. As the $PGE_2$ coating melts or is absorbed, the diameter of the inserted coated portion decreases exposing the rear edge 44 of the rounded tip 42. As a result, when the wand 10 is removed from the urethra, the rear edge 44 acts as a wiper to remove excess $PGE_2$ and carrier from the urethra, thus substantially stopping the delivery of $PGE_2$ to the tissue of the penis. In this manner, the chance of overdose or transfer to the sexual partner during intercourse is greatly reduced or eliminated.

A delivery device 100 for the $PGE_2$ solution shown in FIG. 10 consists of a tube 102 with an integral squeeze bulb 104. The dimensions of the device are chosen so that a unit dose 106 of $PGE_2$ in a suitable solvent is held within the length of the tube and adjacent portion of the squeeze bulb 104 and the squeeze bulb 104 can contain a volume of air 108 such that squeezing of the bulb 104 between two fingers will expel the unit dose. When some or all of the tube is inserted through the external opening of the urethra, squeezing the bulb results in droplet or spray delivery of the tube's contents along at least a portion of the length of the urethra downstream of the inserted end of the tube 102. In one embodiment of the delivery device 100 the tube is from about 1.0 to 3.0 mm in length, has an outer diameter of about 2.5 mm and an inner diameter of about 1 mm. This inner and/or outer diameter may be reduced at the insertable end of the tube to ease insertion and to create a spray of delivered product. The tube is able to contain about 0.01 to 0.03 cc of liquid and the bulb is capable of delivering at least 0.1 cc of air when compressed. However, the tube inner and outer diameter may be smaller and a portion or all of the unit dose may be in the bulb. This allows retention of about 0.01 cc of a liquid in the lumen of the tube. Further, the delivery of the liquid composition is not limited to the use of the device of FIG. 10. One skilled in the art is knowledgeable in the selection of a broad range of catheters for placement within the urethra.

FIG. 11 shows the delivery device 100 residing in a cover 110 which, in cooperation with the structure on the delivery device, acts to retain the dosage within the delivery device during shipping and storage. In particular, threads 112 on the delivery device 100 at the juncture of the squeeze bulb 104 with the tube 102 interact with mating threads 114 on the cover 110 to form a liquid tight seal. Additionally, a soft, flexible cap 116 of a bio-compatible material (non-reactive with the composition enclosed within the dispenser), designed to form a liquid tight seal over the open end of the tube 102, is retained within the cover 110 by a circular shoulder 118. A suitable material for the cap is flexible silicone rubber. The combination of the cap 116 and cover 110 with mating threads 112, 114 keeps the treatment composition from leaking out or evaporating.

Administration of the $PGE_2$ may be accomplished by the transurethral placement of the wand to the desired depth. The $PGE_2$ composition applied to the wand depends on whether a porous or nonporous wand is used. In the case of a porous wand, a liquid solution of the $PGE_2$, a carrier, and possibly an anesthetic and/or a transport adjuvant such as a meltable, swellable or soluble compound, is prepared and the wand is dipped in the solution until sufficient active material is deposited on and in the pores of the wand. This may be supplemented by a less fluid composition, with or without $PGE_2$ applied to the surface of the wand, the surface composition preferably including a lubricant or having lubricating properties.

While transurethral delivery of $PGE_2$ is a highly effective means of treating impotence, an undesirable side effect in some individuals is a sensation of urethral burning or pain and cavernous sinus aching in the genital area. One approach is to add a lubricant and/or a local anesthetic for desensitization thus masking these side effects. In one embodiment, the $PGE_2$, lubricant and anesthetic are all formulated into a convenient cream. This cream may be prepared, for example, by mixing one Upjohn Prostin E® $PGE_2$ suppository together with 10 cc of a lidocaine jelly such as Xylocaine® 2% jelly (available from Astra Pharmaceutical Products) and 50 cc. of a surgical lubricant such as K-Y jelly (available from Johnson & Johnson). Lidocaine HC1, available in a variety of formulations, comprises acetamide, 2-(diethylamino)-N-(2,6-dimethylphenyl) -monohydrochloride.

The amount of lubricant and the amount and concentration of anesthetic can be varied considerably as will be apparent to one of skill in the art. For example, lidocaine jelly can be used having anywhere from about 1% to about 10% and preferably about 2% lidocaine. In general, the anesthetic level can largely be dictated by patient preference, as determined through routine experimentation. Although the incidence of adverse effects with Xylocaine® 2% jelly is very low, caution should be exercised when applying large amounts since the frequency of adverse effects is directly proportional to the total dosage of the local anaesthetic administered. See Astra Pharmaceuticals, product description 021838R11, June 1986; in Physician's Desk Reference, 45th Edition (1991), at p. 628.

A variety of other anesthetic agents can also be used with the formulation of the present invention, as will be appreciated by one skilled in the art. For example, novocaine, procaine, tetracaine or benzocaine may be selected. Patients allergic to para-aminobenzoic acid derivatives such as procaine, tetracaine and benzocaine have not appeared to show cross sensitivity to lidocaine. Lidocaine is also contraindicated in patients with a history of sensitivity to amide type local anesthetics. Xylocaine® 2% jelly also contains methyiparaben, propylparaben and hydroxypropylmethylcellulose, as well as lidocaine; and, therefor, Xylocaine® is contraindicated for patients with known sensitivities to any of these compounds. See Astra Pharmaceuticals, product description 021838R11, June 1986; in Physician's Desk Reference, 45th Edition (1991), at p. 628.

As a result of adding the anesthetic to the $PGE_2$, it has been discovered by the inventor that the effect of the $PGE_2$ treatment is generally less pronounced. Thus, in a lidocaine-containing formulation, the dosage of $PGE_2$ must be increased over that in a non-lidocaine-containing formulation, and more preferably, the $PGE_2$ dosage is preferably doubled in a lidocaine-containing formulation in order to obtain the same effect on impotence. A further negative of adding an anesthetic is that it masks the pain rather than elevating the cause of the pain and may in fact reduce the pleasurable effects of intercourse by reducing tactile sensitivity. Similar dosage increases are required with $PGE_1$ but since $PGE_1$ appears to be less soluble in carriers than $PGE_2$, adequate dosages of $PGE_1$ with anesthetic may not be readily prepared for delivery.

More or less lubricant may be desired depending upon the delivery dose and concentration of the anesthetic jelly. In general, the total volume of the impotence treating unit dose should be no more than 5 cc, and preferably from about 1 cc to no more than about 2 cc due to the inherent capacity of the urethra. Doses of excessive volume can result in painful administration, and also in retrograde migration of the excess formulation into the prostatic urethra or bladder.

Preferably, the total amount of $PGE_2$ contained in a unit dose will be within the range of from about 0.2 mg to about 5.0 mg. Due to differing etiology of erectile dysfunction, and inherent variations across a population in terms of responsiveness to pharmaceutical agents, some routine experimentation may be desired to determine optimum dosages for a given patient or class of patients.

In general, however, doses within the range of from about 0.2 to about 5.0 mg, and preferably from about 0.6 to about 3.6 mg $PGE_2$, have generally proven sufficient in patients in which a response is likely to occur. Although it is not possible to predict with precision what types of patient populations will likely respond to the treatments disclosed herein, certain classes of patients are anticipated to be treatable depending upon the etiology of the condition. For example, patients in whom erectile dysfunction is associated with vascular abnormalities such as atherosclerosis which prevents adequate blood inflow are not likely to respond. Patients in whom the dysfunction is a result of such conditions as diabetes, denervation, or psychological status are expected to be more likely to respond. Where impotence is a result, although undesired, of a surgical procedure, such as a prostatectomy, the efficacy of the treatment may depend on the vascular or nerve damage caused by the surgical procedure. However, clinical trials have shown the $PGE_2$ formulation is an effective treatment in many patients who show no, or an inadequate response to $PGE_1$ or Viagra®.

In the antidotal or priapism treating $PGF_{2\alpha}$ formulation, the $PGF_{2\alpha}$ will generally be present in an amount within the range of from about 5 to about 50 μg per 1 cc of formulation, preferably within the range of from about 8 to 20 μg/cc and more preferably about 12 μg/cc. As with the $PGE_2$ formulation, optimum dosage for a given patient can be determined through routine experimentation.

It has now been discovered that the burning, aching or cramping sensation can be eliminated without the use of an anaesthetic agent and the commensurate increase in $PGE_2$ to obtain the same effect. As described above, $PGF_{2\alpha}$ reverses the effect of $PGE_2$, i.e. terminates an erection. It has now been found that mixing small amounts of $PGF_{2\alpha}$ with $PGE_2$ eliminates the burning or aching experienced by some individuals when $PGE_2$ is used alone. It has further been discovered that, unlike the addition of an anaesthetic to $PGE_2$, adding $PGF_{2\alpha}$ in small doses does not reduce the beneficial effects of $PGE_2$, alleviates the cause of the pain rather than masking it and does not reduce the desirable sensory effects of intercourse. Further, additional amounts of $PGE_2$ are generally not required to obtain the same beneficial effects.

A suitable $PGE_2$ composition to eliminate the undesirable burning and aching sensation without noticeably reducing the impotence treatment effect of the $PGE_2$ includes from about 0.1 μg to about 2.0 μg of $PGF_{2\alpha}$. Below about 0.1 μg the burning and aching may persist and above about 2 μg and erection may occur more slowly and may not be adequate for intercourse. A preferred composition includes about 0.25 μg of $PGF_{2\alpha}$ for each milligram of $PGE_2$.

It has been further discovered that addition of phentolamine mesylate

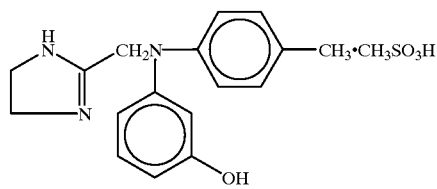

to $PGE_2$ increases the beneficial characteristics of the $PGE_2$ impotence treatment; namely rigidity and longevity of the erection. However, the urethral burning and cavernous sinus aching still persists. The addition of $PGF_{2\alpha}$ to the combination, as in the case of addition to $PGE_2$, eliminates this undesirable side effect without reducing the enhanced benefits of the use of the phentolamine mesylate. A typical composition to produce an erection effective for intercourse comprises 1.0 mg $PGE_2$, 0.25 μgm $PGF_{2\alpha}$ and 0.25 mg phentolamine mesylate in about 0.2 cc of a suitable carrier, such as sterile water. Smaller or larger doses, volumes or variations on the ratios of components may be used to adjust to particular patient response and disease etiology.

Any of several different delivery systems may be utilized in accordance with the method of the present invention. For example, a fluid, cream, gel system or solid suppository can be used and the carrier can be absorbed directly, or allowed to be expelled following sufficient dwell time which may be controlled by occluding the distal end of the urethra.

Alternatively, more solid delivery vehicles may be used such as an ovoid or rod-shaped suppository. Suppositories can be formulated from any of a variety of materials which exhibit sufficient physical integrity to permit transurethral insertion and which will then permit delivery of the medication. Once installed, the structural component of the suppository may break down under the influence of body heat. An advantage of applying the meltable composition to the surface of the wand is that the wand can be removed once the desired erection is achieved, thus terminating drug delivery, a procedure not afforded by suppository products. Alternatively, the $PGE_2$ composition placed in the pores of the wand can be protected until delivery by applying a sealing material on the surface of the wand, the sealing material melting or dissolving when placed within the urethra. As a further alternative, materials can be used which will dissolve in an aqueous environment at a pH within the range of that typical of the urethra. One suitable composition is a mixture of glycerides of fatty acids such as that used with the Prostin $E_2$® product. Other suitable compositions include various cellulose based materials such as hydroxypropylmethylcellulose or collagen compositions which can be prepared as a fluid water-based material, a viscous solution, a gel or a water swellable dry coating. One skilled in the art can identify numerous physiologically acceptable water soluble materials or hydrogels which can be used for the purposes set forth above.

The above noted burning sensation is also experienced when using $PGE_1$. It has been found that addition of $PGF_{2\alpha}$ has substantially the same effect when added to $PGE_1$ in a percentage to total dosage equivalent to that used with $PGE_2$.

As a further alternative, a variety of drug delivery vehicles may be used which neither dissolve nor break down in the environment of the urethra. Relatively rigid rod-shaped delivery vehicles may be fashioned from materials having a microporous structure for the time release of entrapped pharmaceutical.

A major advantage of transurethral insertion of a wand is that it can be inserted for a predetermined period of time and then removed following delivery of an efficacious amount of drug. The removable time release delivery structure has the added advantage of providing a range of flexibility in the total delivered dose. Thus, the patient, by leaving the implant in place for relatively shorter or longer periods of time, can optimize the dose within a preset maximum range. A particular advantage of the cream, gel, or solution over prior disclosed pellets of drug containing compositions placed in the urethra is that the compositions disclosed herein can be readily dispersed along the length of the urethra allowing delivery through a large area of tissue surface, thus reducing or eliminating the undesirable effects of delivering high dose concentrations to a very localized area, including slower dispersion, localized discomfort and less pronounced effectiveness.

Particular embodiments of the present invention will be described in the Examples which follow.

EXAMPLE I

Preparation of Intraurethral $PGE_2$ Cream

A batch of $PGE_2$ cream was prepared by mixing 40 mg of $PGE_2$ suppository (obtained as the "Prostin $E_2$" suppository from the Upjohn Company) with 10 cc of 2% Xylocaine jelly and 50 cc of K-Y surgical lubrication jelly (hydroxyethyl-cellulose, obtained from Johnson & Johnson). Mixing was accomplished by stirring until the mixture appeared homogenous upon visual inspection. The result was a $PGE_2$ cream having approximately 1.3 mg of $PGE_2$ per 2 cc of cream. A portion of the cream was reserved for placement directly into the urethra while a second portion was applied to the surface of a wand. Approximately 2 cc of cream was applied to a 4 cm of the insertable length of a porous wand to produce a coated product 5 mm in diameter. This can be readily inserted and removed from the urethra.

EXAMPLE II

Preparation of Intraurethral $PGE_2$ Gel

The homogenecity of a bath of $PGE_2$ is ensured by inclusion of a methylene blue marker. One 20 mg $PGE_2$ suppository ("Prostin $E_2$" from the Upjohn Company) is sliced into thin slices and allowed to soften at room temperature for 15 minutes. A small drop of 1% methylene blue solution (American quinine, Shirley, New York) is placed onto each slice to serve as a marker for homogenicity. The softened slices are thereafter geometrically mixed with the contents of a 56.7 gram tube of K-Y jelly to yield a homogenous mixture, as evidenced by blue color uniformity. The theoretical content of the final product is approximately 0.68 milligrams of $PGE_2$ per 2 cc of gel. A portion of the cream was reserved for placement directly into the urethra while a second portion was applied to the surface of a wand. The gel was applied to 4 cm of the insertable length of a porous wand to produce an insertable product having a 3.0 to 5.0 mm diameter for insertion in the male urethra.

EXAMPLE III

Preparation of Lipid Based Intraurethral $PGE_2$ Cream

A batch of $PGE_2$ cream in cocoa butter is prepared by placing one 20 mg. $PGE_2$ suppository (Prostin $E_2$ by the Upjohn Company) into a porcelain evaporating dish and is melted in a 37° C. water bath. Shredded cocoa butter is added to the melted suppository with stirring to bring the total mass to approximately 20 grams. As the melting continues, the temperature of the mixture is kept at or below about 33° C. Higher temperatures are to be avoided, as they have been reported to cause the crystalline form of the cocoa butter to change, resulting in aberrations in bioavailability. Transformations in the crystalline form of the cocoa butter are visually observed as a change from opalescent to transparent. After complete melting, the mixture is stirred thoroughly and a first portion poured into suppository molds. The material is thereafter allowed to cool at room temperature for about 15 minutes, and thereafter is placed in the refrigerator to facilitate further solidification. The suppositories may thereafter be removed from the mold, individually packaged and placed in refrigerated storage under anhydrous conditions.

A second portion of the mixture was applied to 4 cm of the insertable length of a porous wand which was about 2 mm in diameter using a tubular mold. The material is thereafter allowed to cool at room temperature for about 15 minutes, and thereafter is placed in the refrigerator to facilitate further solidification in to 5 mm diameter coated wands. The coated wands are thereafter removed from the mold, individually packaged and placed in refrigerated storage under anhydrous conditions.

EXAMPLE IV

Administration of Intraurethral $PGE_2$ Cream

Two cc of the $PGE_2$ cream from Example I was instilled into the urethral meatus of each of 10 impotent male patients between the ages of 50 and 70, using a syringe. The cream was massaged down the urethra, and then the distal end of the urethra was occluded for 5 minutes by manual pressure.

EXAMPLE V

Administration of Intraurethral $PGE_2$

Wands containing about 2 cc of a $PGE_2$ composition prepared in accordance with Examples I–III placed within the urethra of males would be expected to cause full tumescence suitable for intercourse in a majority of the test subjects within about 15 minutes of placement of the wand at which time the wand can be removed, such removal terminating the delivery from the wand of the $PGE_2$, except for small amounts which remain on the urethral mucosa.

EXAMPLE VI

Efficacy of $PGE_2$ Cream in Treating Human Erectile Dysfunction

The effect of administration of $PGE_2$ cream and the coated wand, prepared and administered in accordance with the procedures of Examples I and IV, was observed. After 15 to 30 minutes, treatment response was rated as no penile tumescence, partial tumescence or full tumescence.

As a result with the cream, two of the ten men treated had no response, six had partial tumescence, and two had full tumescence. Thus, 80% of the men treated showed at least partial penile tumescence in response to the intraurethral $PGE_2$ cream. Those treated with the cream treated wand would be expected to have a similar response.

EXAMPLE VII

Efficacy of Lower Concentrations of $PGE_2$ Cream in Treating Human Erectile Dysfunction $PGE_2$ cream was prepared and administered in accordance with the procedures of Examples I and IV, except that a 20 mg $PGE_2$ suppository was used instead of a 40 mg suppository. This cream contained approximately 0.7 mg of $PGE_2$ per 2 cc of cream. Two cc of cream was used to treat each of ten impotent men between the ages of 50 and 70. After 15 to 30 minutes, treatment response was rated as no penile tumescence, partial tumescence, or full tumescence.

As a result, four of the ten men treated had no response, two had partial tumescence, and four had full tumescence. Thus, even using lower concentrations of $PGE_2$, 60% of the men treated showed at least partial penile tumescence in response to the intraurethral $PGE_2$ cream. Those treated with the cream treated wand would be expected to have a similar response.

EXAMPLE VIII

Intraurethral Administration of a $PGE_2$ Hydrogel Composition

A wand carrying approximately 5 mg of $PGE_2$ in a hydrogel polymer carrier was placed into the urethral meatus of a 65 year old impotent male patient.

An effective erection resulted after 15 minutes at which point the wand was removed. Erection was sufficiently effective for intercourse. Detumescence commenced at approximately 1 hour after removal. Some $PGE_2$ remained in the wand after removal, the amount not being ascertained. As a result, an amount of $PGE_2$ less than 5 mg was delivered.

EXAMPLE IX

Use of $PGF_{2\alpha}$ to Counteract Effects of Administration of $PGE_2$

Priapism resulting from the use of an excess amount of $PGE_2$ has been determined to be reversible or treatable through the application of an effective antidotal amount of a 15 methyl substituted prostaglandin $F_{2\alpha}$ containing formulation. In addition, it is anticipated that priapism from a variety of other treatments for impotence ($PGE_1$ or Viagra®) will be similarly treatable.

An antidotal formulation is prepared by mixing approximately 250 micrograms of prostaglandin $F_{2\alpha}$ obtained as Hemabate, marketed by Upjohn, in approximately 20 cc of K-Y jelly. Mixing is accomplished manually until visual observation reveals a homogenous composition. A dose of approximately 1 cc of the foregoing formulation was instilled into the urethra of an erect penis, to reverse the results of the $PGE_2$ treatment in accordance with the present invention. Following delivery of the $PGF_{2\alpha}$ there is immediate relief of pain and within 5 minutes detumescence resulted.

EXAMPLE X

Use of a $PGE_2/PGF_{2\alpha}$ Combination to Treat Impotence

Freeze dried $PGE_2$ was obtained from Chinoin Pharmaceutical and Chemical Works Co. Ltd., Budapest, Hungary. Three different solutions were prepared with $PGE_2$ concentration being 0.5, 1.0 or 1.5 mg/0.1 cc of physiological saline. Samples were also prepared with the addition of $PGF_{2\alpha}$ to the $PGE_2$ solution in the amount of 0.25 µg/1.0 mg $PGE_2$ The several different solutions were instilled into the urethra of a normally impotent male at a distance of at least about 1 cc from the external opening of the urethra. An erection suitable for sexual intercourse occurred within about 3 to 5 minutes after placement of the solution and the erection lasted about 1 hour. In several instances the use of the $PGE_2$ solution resulted in a noticeable burning or aching feeling within the erect penis. No burning or aching was experienced in the solutions containing the $PGF_{2\alpha}$ and the erectile effect and sustainability of the erection appeared to the treated individual to be undistinguishable from that of a control comprising a similarly prepared solution without the addition of the $PGF_{2\alpha}$. The only noticeable difference was the elimination of the burning sensation along the urethra encountered with the control solution. The 0.25 µg/1 mg concentration was found to be effective in most instances and the lesser concentrations were effective in fewer patients or produced a less satisfying result.

It has been further discovered that $PGE_2$, when applied to the mucous membrane of the introitus, labia minora, and/or clitoris of female external genitalia can also cause a physiological response reported to enhance sexual relations by causing engorgement of the treated tissue with blood in a manner similar to the creation of an erection in a male.

$PGE_2$ prepared in a cream in the same manner as described above, when applied to the external female genitalia, increases blood flow to the tissue treated which, in turn, causes a temporary swelling of the external genitalia to which applied and an enhanced sensitivity to external stimuli. A typical response is engorgement of the genitalia, redness, swelling and increased sensitivity typical of a normal response in an aroused female, the response occurring within about 10–15 minutes following application. A similar response results from use of $PGE_2$ dissolved in a liquid carrier, such as water, when applied onto the genitalia or dispensed from a spray dispenser onto the external genitalia. $PGE_2/PGF_{2\alpha}$ can also be used with a similar result. It is also believed that the addition of phentolamine mesylate will also have a beneficial effect.

In a study of several women using $PGE_2$ prepared in a liquid comprising 1.0 mg $PGE_2$ and 0.25 µg $PGF_{2\alpha}$ in KY liquid (a water soluble, physiologically acceptable topical composition commercially available from Johnson & Johnson as a sexual lubricant) the women reported:

1. an increased pleasurable genital sensation
2. shortened time needed for foreplay to gain desirable stimulation
3. a higher incidence of orgasmic response reached within a shorter time period of stimulation and/or intercourse, and
4. a tightening of the external genitalia resulting in an increased stimulation on the erect penis of the sexual partner.

It has also been found that intra-urethral instillation of $PGE_2$ in women can enhance sexual response. Two women received a 0.5 mg dose of the $PGE_2$ with $PGF_{2\alpha}$ formula used in men in Example X above. The dose was administered using the same delivery system shown in FIG. 11. No urethral burning or other side effect were indicated. In comparison with vaginal intercourse without the $PGE_2$/$PGF_{2\alpha}$, both women reported increased sexual arousal and ease of orgasm.

Some leakage of the solution from the urethra occurred in one individual, but only after sexual arousal had begun (approximately 3 minutes). It is believed this leakage can be eliminated by use of a gel formulation.

It was highly unexpected that intra-urethral $PGE_2$ would have a beneficial effect in women since they have no cavernous sinus. However, a basis for the unexpected efficacy may be due to the existence of the "G-spot".

Dr. Ernst Grafenberg was the first to describe an erogenous zone located beneath the anterior vaginal wall, in an article published in "The International Journal of Sexology" in 1950. His name has come to be associated with this area in both medical and lay publications, where it is often referred to simply as "the G-spot". This area is about 2 cm deep to the pubic bone and is approximately the size of a small olive. It is soft and poorly outlined at rest. However, massage of this "G-spot" causes it to swell and become hard and well defined. A distinct pleasurable sensation is experienced by women, and orgasm appears to be associated with deeper pelvic contractions and to be more pleasurable from "G-spot" stimulation than orgasm resulting from clitoral stimulation alone.

The "G-spot" is believed by many to be analogous to the mail prostate, and this is discussed in a review article by J. Lowndes Sevely and J. W. Bennet in the *Journal of Sex Research*, February 1987, entitled "Concerning female ejaculation and the female prostate".

Accordingly, it is believed that urethral placement of the $PGE_2$/$PGF_{2\alpha}$ composition permeates the female urethral wall and acts on the "G-spot" to provide sensations at least comparable to manual stimulation of that portion of the female anatomy. Also the response in females from urethral delivery of $PGE_2$ and $PGE_2$/$PGF_{2\alpha}$ are believed to also result from urethral delivery of $PGE_1$ and $PGE_1$/$PGF_{2\alpha}$ compositions.

Although this invention has been described in terms of certain preferred embodiments, other embodiments that are apparent to those of ordinary skill in the art are also within the scope of the invention. In particular, analogs or derivatives of $PGE_2$ and $PGF_{2\alpha}$ which do not affect the basic functionality of those molecules as described herein are also considered within the scope of the present invention. Accordingly, the scope of the invention is intended to be defined only by reference to the appended claims.

What is claimed is:

1. A method of enhancing sexual arousal in a human female comprising the administration to mucosal tissue of the genitalia or urethra of said female a unit dose of a mixture of
    a) a prostaglandin, said prostaglandin selected from the group consisting of $PGE_1$, $PGE_2$, a physiologically acceptable salt thereof, a physiologically acceptable ester thereof, and mixtures thereof, and
    b) $PGF_{2\alpha}$, a physiologically acceptable salt thereof, or a physiologically acceptable ester thereof, or a mixture thereof,
        the mixture of a) and b) above carried in a readily dispersable pharmaceutically acceptable delivery medium.

2. The method of claim 1 wherein the mixture of readily dispersable pharmaceutically acceptable delivery medium is applied to the mucosa of the external genitalia of the female.

3. The method of claim 2 wherein the unit dose contains from about 0.5 μg to about 5.0 μg of $PGF_{2\alpha}$.

4. The method of claim 2 wherein the unit dose contains about 1 μg of $PGF_{2\alpha}$ for each milligram of the prostaglandin.

5. The method of claim 2 wherein the unit dose contains from about 0.5 μg to about 5.0 μg of $PGF_{2\alpha}$ and about 1 μg of $PGF_{2\alpha}$ for each milligram of $PGE_2$.

6. The method of claim 1 wherein the mixture of readily dispersable pharmaceutically acceptable delivery medium is placed within the urethra of the female.

7. The method of claim 6 wherein the unit dose contains from about 0.5 μg to about 5.0 μg of $PGF_{2\alpha}$.

8. The method of claim 6 wherein the unit dose contains about 1 μg of $PGF_{2\alpha}$ for each milligram of the prostaglandin.

9. The method of claim 6 wherein the unit dose contains from about 0.5 μg to about 5.0 μg of $PGF_{2\alpha}$ and about 1 μg of $PGF_{2\alpha}$ for each milligram of $PGE_2$.

10. A composition for enhancing sexual arousal of a female individual comprising a mixture of
    a) a prostaglandin selected from the group consisting of $PGE_1$, $PGE_2$, a physiologically acceptable salt thereof, a physiologically acceptable ester thereof, and a mixture thereof, and
    b) $PGF_{2\alpha}$, a physiologically acceptable salt thereof, or a physiologically acceptable ester thereof, or a mixture thereof
        the mixture of a) and b) above carried in a pharmaceutically acceptable delivery medium readily dispersable to the genital mucosal tissue or urethra of the of the individual.

11. The composition of claim 10 wherein a unit dose thereof contains from about 0.5 μg to about 5.0 μg of $PGF_{2\alpha}$.

12. The composition of claim 10 wherein a unit dose thereof contains about 1.0 μg of $PGF_{2\alpha}$ for each milligram of the prostaglandin.

13. The composition of claim 12 wherein a unit dose comprises 0.1 cc to 0.5 cc of a solution containing from about 0.2 to about 5.0 mg of the prostaglandin.

14. The composition of claim 13 wherein the unit dose comprises 0.1 cc to 0.5 cc of a solution containing from about 0.5 to about 3.6 mg of the prostaglandin.

15. The composition of claim 14 wherein the unit dose thereof contains about 1.0 μg of $PGF_{2\alpha}$ for each milligram of prostaglandin.

16. The composition of claim 15 wherein the unit dose thereof contains about 1.0 μg of $PGF_{2\alpha}$ for each milligram of $PGE_2$.

17. The composition of claim 13 wherein the unit dose comprises 0.1 cc of solution containing from about 0.5 to about 1.0 mg of $PGE_2$.

* * * * *